US010302601B2

(12) United States Patent
McGill et al.

(10) Patent No.: US 10,302,601 B2
(45) Date of Patent: May 28, 2019

(54) GAS CHROMATOGRAPHIC "IN-COLUMN" SPECTROSCOPIC ANALYSIS

(71) Applicant: The United States of America, as represented by the Secretary of the Navy, Washington, DC (US)

(72) Inventors: R. Andrew McGill, Lorton, VA (US); Robert Furstenberg, Largo, MD (US); Viet K. Nguyen, Gaithersburg, MD (US); Chris Kendziora, Burke, VA (US); Michael Papantonakis, Washington, DC (US); Todd H. Stievater, Arlington, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 42 days.

(21) Appl. No.: 15/464,378

(22) Filed: Mar. 21, 2017

(65) Prior Publication Data
US 2017/0284976 A1    Oct. 5, 2017

Related U.S. Application Data

(63) Continuation of application No. 14/208,088, filed on Mar. 13, 2014, now Pat. No. 9,599,567.
(Continued)

(51) Int. Cl.
*G01N 30/02* (2006.01)
*G01N 30/60* (2006.01)
(Continued)

(52) U.S. Cl.
CPC ......... *G01N 30/02* (2013.01); *G01N 21/0332* (2013.01); *G01N 21/3504* (2013.01);
(Continued)

(58) Field of Classification Search
CPC .. G01N 21/7746; G01N 21/552; G01N 30/74; G01N 21/0332; G01N 21/3504; G01N 21/658; G01N 30/6082
(Continued)

(56) References Cited

U.S. PATENT DOCUMENTS

2006/0120683 A1*  6/2006  Kamp ................... B01D 15/22
                                                    385/141
2006/0210441 A1*  9/2006  Schmidt ................ G01N 30/20
                                                    422/89
(Continued)

*Primary Examiner* — Natalie Huls
*Assistant Examiner* — Monica S Young
(74) *Attorney, Agent, or Firm* — US Naval Research Laboratory; Rebecca L. Forman

(57) ABSTRACT

A chemical detector for rapid, simultaneous detection of multiple chemicals including chemical warfare agents, toxic industrial chemicals, and explosives having one or more gas chromatography columns each with a chemosorbent or a chemo-reactive stationary phase and an infrared-transparent base, a bright infrared light source, a mechanism to direct the light source to any point along any of the columns, and an infrared sensor. Another disclosed detector has one or more gas chromatography columns each on the surface of a substrate having at least one infrared-transparent waveguide pattern, a bright infrared light source, and at least one ring resonator for each column, where each ring resonator is coated with a chemosorbent or a chemo-reactive stationary phase, and where each ring resonator spectroscopically probes the stationary phase. Also disclosed are the related methods for chemical detection.

13 Claims, 10 Drawing Sheets

Related U.S. Application Data

(60) Provisional application No. 61/788,723, filed on Mar. 15, 2013.

(51) Int. Cl.
| | | |
|---|---|---|
| *G01N 21/77* | (2006.01) | |
| *G01N 30/74* | (2006.01) | |
| *G01N 21/552* | (2014.01) | |
| *G01N 21/3504* | (2014.01) | |
| *G01N 21/03* | (2006.01) | |
| *G01N 21/39* | (2006.01) | |
| *B01J 20/281* | (2006.01) | |
| *G01N 21/65* | (2006.01) | |
| *G01N 21/47* | (2006.01) | |

(52) U.S. Cl.
CPC .......... *G01N 21/39* (2013.01); *G01N 21/552* (2013.01); *G01N 21/7746* (2013.01); *G01N 30/48* (2013.01); *G01N 30/6034* (2013.01); *G01N 30/74* (2013.01); *G01N 21/658* (2013.01); *G01N 30/6082* (2013.01); *G01N 2021/4761* (2013.01); *G01N 2030/025* (2013.01)

(58) Field of Classification Search
USPC .......................................................... 73/23.37
See application file for complete search history.

(56) References Cited

U.S. PATENT DOCUMENTS

| | | | |
|---|---|---|---|
| 2009/0189064 A1* | 7/2009 | Miller | G01N 27/624 |
| | | | 250/282 |
| 2010/0044570 A1* | 2/2010 | McGill | G01N 21/71 |
| | | | 250/338.5 |
| 2011/0271738 A1* | 11/2011 | McGill | G01N 21/64 |
| | | | 73/23.41 |

* cited by examiner

GAS CHROMATOGRAPHIC "IN-COLUMN" SPECTROSCOPIC ANALYSIS

PRIORITY CLAIM

The present application is a continuation application claiming the benefit of U.S. application Ser. No. 14/208,088, filed on Mar. 13, 2014 by R. Andrew McGill et al., entitled "Gas Chromatographic 'In Column' Spectroscopic Analysis," which was a non-provisional application claiming the benefit of U.S. Provisional Application No. 61/788,723, filed on Mar. 15, 2013 by R. Andrew McGill et al., entitled "Gas Chromatographic 'In Column' Spectroscopic Analysis," the entire contents of each are incorporated herein by reference.

BACKGROUND OF THE INVENTION

Field of the Invention

The present invention relates generally to IR detectors and, more specifically, to IR detectors using a gas chromatographic in-column spectroscopy.

Description of the Prior Art

A significant remaining challenge today in the chem-bio defense community is the simultaneous and reliable detection of a large number of chemicals and types covering all the chemical warfare agents (CWAs) and toxic industrial chemicals (TICs) in a "point" detection application. The development of a detector with suitable analytical fidelity can be reduced to the development of strategies or techniques to best exploit differences in analyte physicochemical properties.

IR spectrophotometry is an established lab fixture providing rich molecular information content, however performance is degraded for complex mixtures and traditional hardware suffers from relatively low sensitivity.

Fan et al. have reported in-column sensing. U.S. Patent Application Publication 2013/0169970 by Fan et al. (Jul. 4, 2013) and Reddy et al., "Rapid, sensitive, and multiplexed on-chip optical sensors for micro-gas chromatography," *Lab Chip*, 12, 901-05 (2012). However, Fan et al. perform non-spectroscopic sensing and focus on measuring refractive index changes in a sorbent coated sensor embedded in the gas chromatography (GC) column. This approach lacks the selectivity provided by an IR absorption spectroscopic sensing approach. Moreover, this approach uses discrete sensors that do not sense at all points along the column.

BRIEF SUMMARY OF THE INVENTION

The aforementioned problems are overcome in the present invention which provides a chemical detector for rapid, simultaneous detection of multiple chemicals including chemical warfare agents, toxic industrial chemicals, and explosives having one or more GC columns each with a chemosorbent or a chemo-reactive stationary phase and an infrared-transparent base or column, a bright infrared light source, a mechanism to direct the light source to any point along any of the columns, and an infrared sensor. When multiple columns are used, the columns may be operated in parallel. In some configurations a single column with different regions employing different sorbent stationary phases is advantageous for selectivity and sensitivity purposes. In a preferred embodiment, at least one stationary phase comprises a carbosilane polymer with hydrogen bond (HB) acidic functionalization. Other examples include HB basic polymers, polar, polarizable and non-polymer polymers and organometallic materials offering transition metal coordination site chemistries. The infrared-transparent base can be an attenuated total reflection (ATR) crystal. The bright infrared light source can be a tunable infrared quantum cascade laser (QCL). The infrared sensor can be preceded by an integrating sphere to remove the changes in the infrared signal due to slight direction changes of the laser beam when examining different points along the column. Alternatively, an IR focal plane array (FPA) can be used to image all the channels simultaneously, as the laser wavelengths are tuned. In this configuration, the laser light would illuminate all of the columns, as opposed to being focused as is the case when using a single element detector. The detector system can also include a preconcentrator device before or at the head of the GC columns. Another disclosed detector system includes one or more GC columns each on the surface of a substrate having at least one infrared-transparent waveguide pattern, a bright infrared light source, and one or more ring resonators for each column, where each ring resonator is coated with a chemosorbent or a chemo-reactive stationary phase, and where each ring resonator spectroscopically probes the GC stationary phase. Also disclosed are the related methods for chemical detection.

The present invention allows the detection of a wide range of chemicals with a wide range of vapor pressures present in the air as complex mixtures. This has only been previously possible with relatively large instruments, whereas the present invention allows small hand-held configurations to be realized. The present invention allows analyses to be made at the head of the GC column in a preconcentrator or collection device and, while analytes progress along a GC column, by probing an IR transparent side of the column, rather than having to wait for end of column elution. This reduces unnecessary wait time and increases sensitivity by avoiding unnecessary peak spreading. This allows detections to be monitored during column separations and an alarm to be achieved before end of column elution. The optical interrogation allows rapid analysis at any point along different columns by directing the light appropriately. By combining the elements of column separation and IR spectroscopy analysis (with a tunable bright IR source) and arrays of stationary GC phases with IR sensors, the present invention offers the potential for high analyte discrimination with short analysis times. The present invention incorporates an ultra-bright monochromatic tunable IR source (e.g. QCL) which allows selective probing of analytes. In contrast, conventional IR spectroscopy uses a weak IR source generating IR light over many wavelengths which provides low sensitivity and poor selectivity derived from the incident IR light. Analysis occurs as analytes propagate along a column, but conventional gas chromatography detectors may also be used at the end of the column. So detection algorithms will be responsible for analyzing data during analyte propagation through the column and possibly for data collected from a sensor at the end of the column. Algorithms include, but are not limited to: least squares regression techniques (including non-negative LS), SVM, matched and adaptive sub-space detectors, spectral match filtering, adaptive boosting, neural networks, PCA, ICA, and greedy pursuit algorithms. The data may take the form of hyperspectral image cubes, in which case a method specific to that form (e.g., the sub-space detector) should be used.

These and other features and advantages of the invention, as well as the invention itself, will become better understood

BRIEF DESCRIPTION OF THE DRAWINGS

FIG. 6 shows an ATR-based sensor using diffraction grating.

FIG. 8 shows a Raman-based sensor.

DETAILED DESCRIPTION OF THE INVENTION

The purpose of the present invention is to provide a general framework to optimize molecular affinity and analyte discrimination for a large group of chemicals by employing a set of sorbent chemistries, chromatographic separations and "in-column" detections using infrared light to probe and access molecular information.

Figure 1:
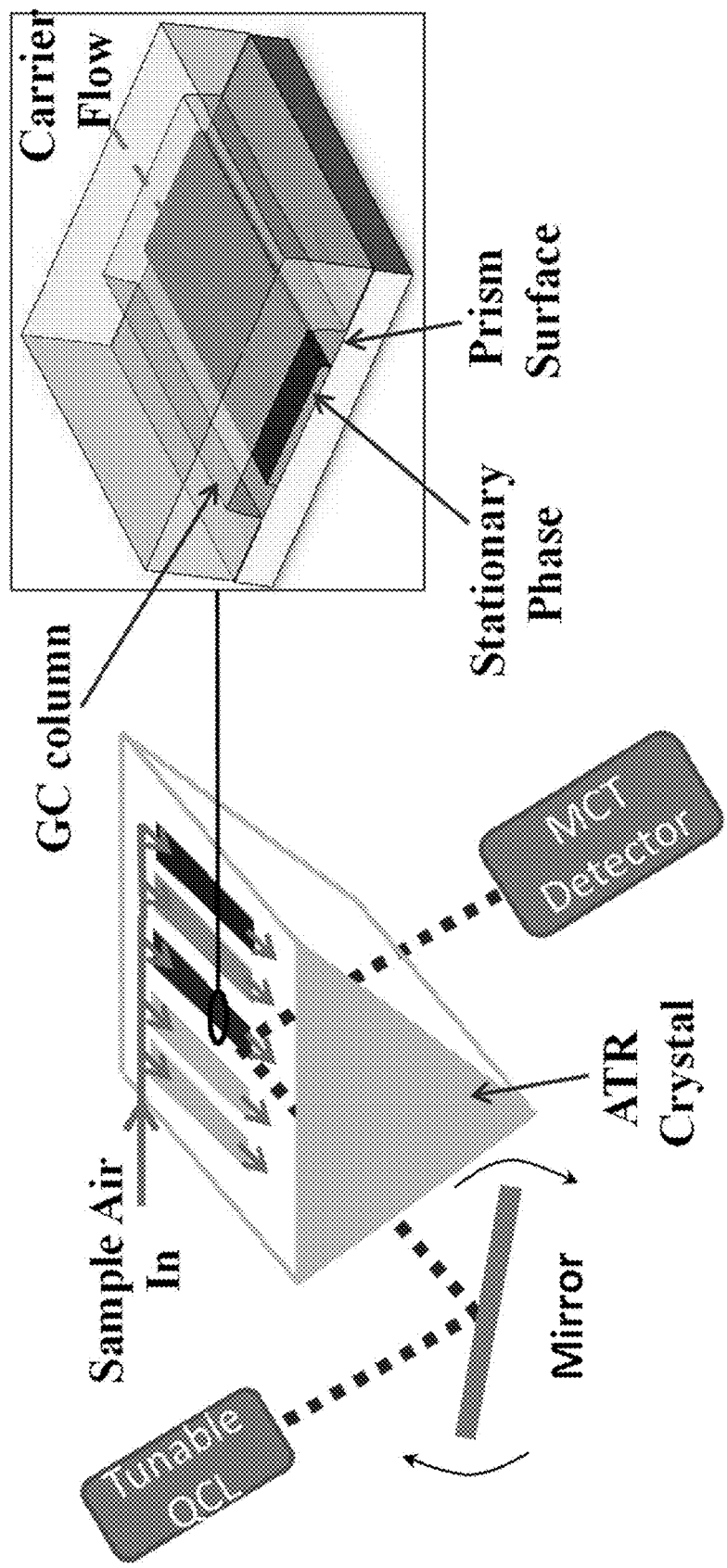
FIG. 1 shows an array of GC columns deposited on a prism used in an ATR configuration and probed by a tunable ultra-bright IR QCL light source to measure "in-column" IR absorption spectra as a function of incident wavelength and location along the GC column.
Figure 2:
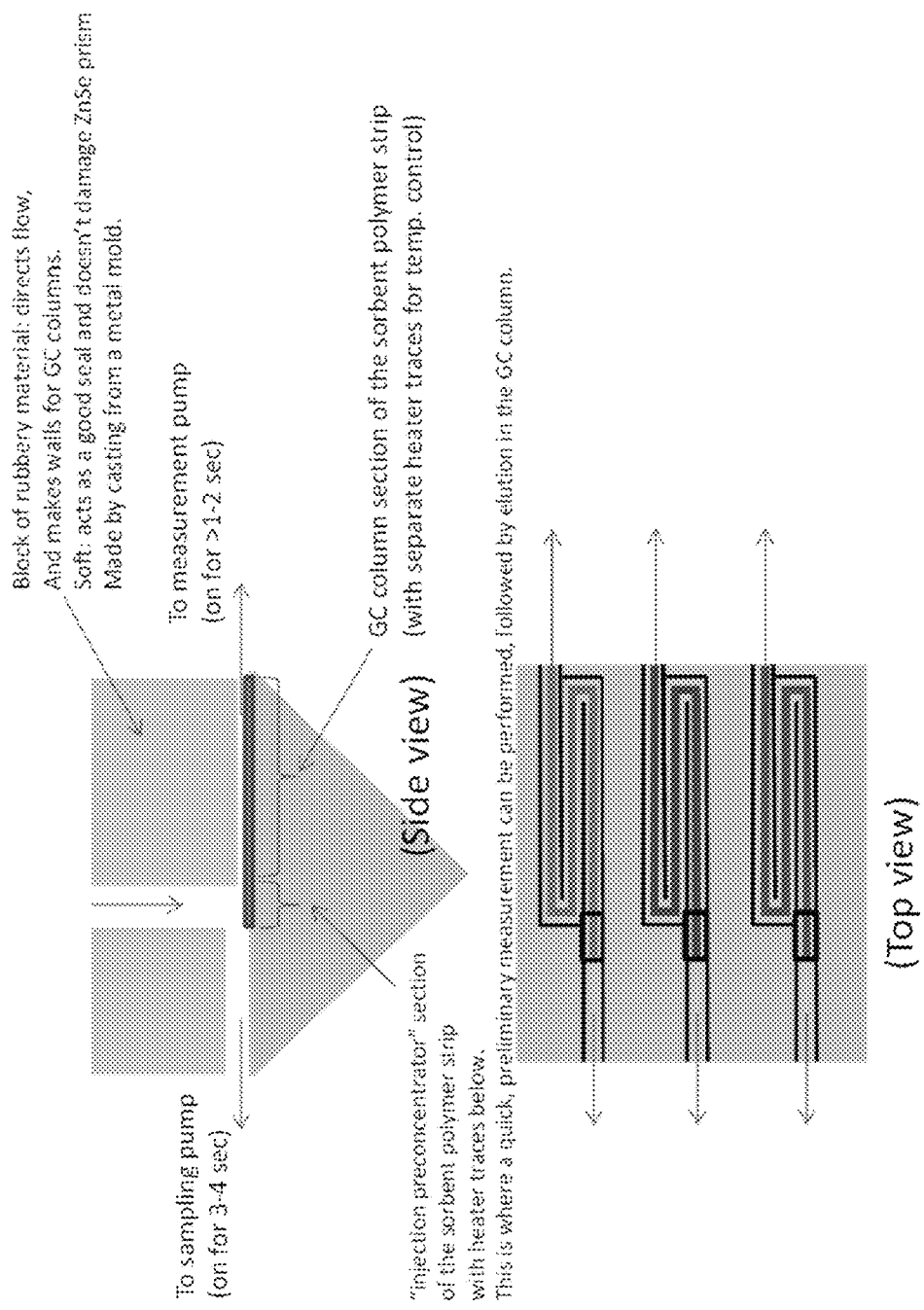
FIG. 2 shows an array of serpentine GC columns deposited on an ATR crystal. Analyte carried by carrier gas flow is trapped at the head of each column in a preconcentrator section. This may be a relatively thick sorbent coated area and may be separately temperature controlled from the rest of the GC column with a built-in micro heater and heated to release analyte for GC injection. The stationary phase trace may be capped with a variety of passivated structures to seal with the ATR crystal surface and allow carrier gas flow along the stationary phase length.

The analytical separation power of multimodal gas chromatographic (GC) columns, operated in a parallel format, is combined with IR absorption spectroscopy used to monitor analytes during their chromatographic progression "in-column". Sensitivity and selectivity are augmented by incorporating selective sorbents as GC stationary phases to target CWAs and TICs through reversible binding analyte or chemical reactions between an analyte and a stationary phase. An ultra-bright tunable IR laser, such as a quantum cascade laser (QCL) or other bright IR light source provides a dramatic increase in photon density to probe the chemistries involved. By design, IR interrogation and analyte detection is enabled at all points along a column during the GC analysis. As shown in FIG. 1, a moveable mirror can direct the infrared light source. Also, a focusing lens and mirror can direct the light source. QCL spot size may be localized to the stationary phase or column width and monitored with a single element IR sensor as a function of column scan, or a larger QCL spot size can bathe the entire GC array and an arrayed IR sensor can simultaneously monitor all column points. To achieve this, an IR-transparent column base (e.g. polished ATR crystal) is incorporated in the column design and bonded to a bridging structure with a gas tight flow manifold (FIGS. 1 and 2). For less complicated analyte samples, suitable high detection fidelity may be achieved at or near a GC column inlet whereas for more complex samples this may occur further along a column with additional separation. In-column analyses allow optimum detection to be achieved or a preliminary rapid detection call to be made without waiting for complete column elution with subsequent detections along a column providing increasing detection confidence if further separation of analytes is achieved.

IR Spectroscopic Properties

Figure 3A:
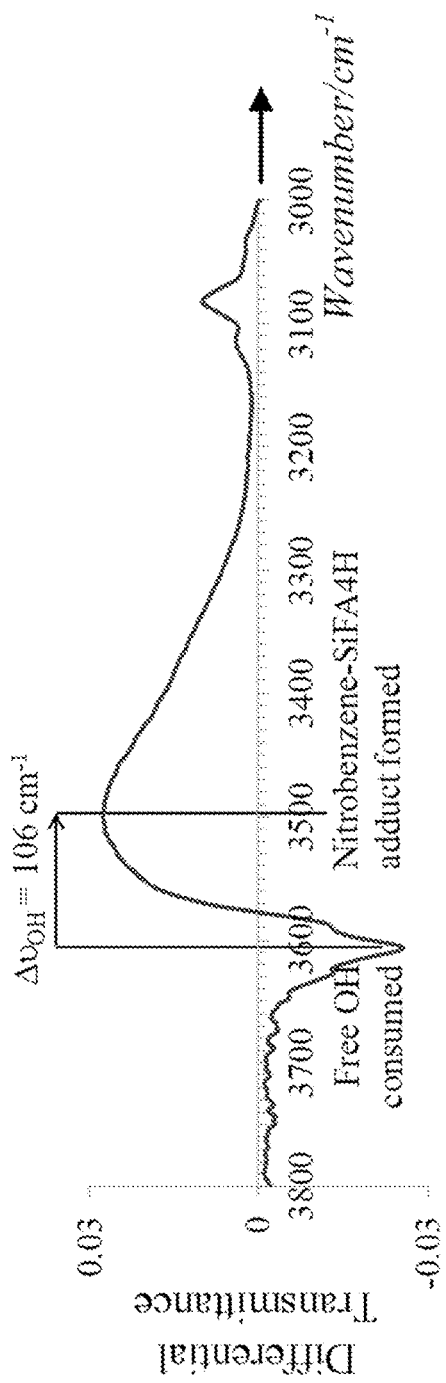
FIG. 3A shows a differential FTIR spectra for SiFA4H-Nitrobenzene HB adduct.
Figure 3B:
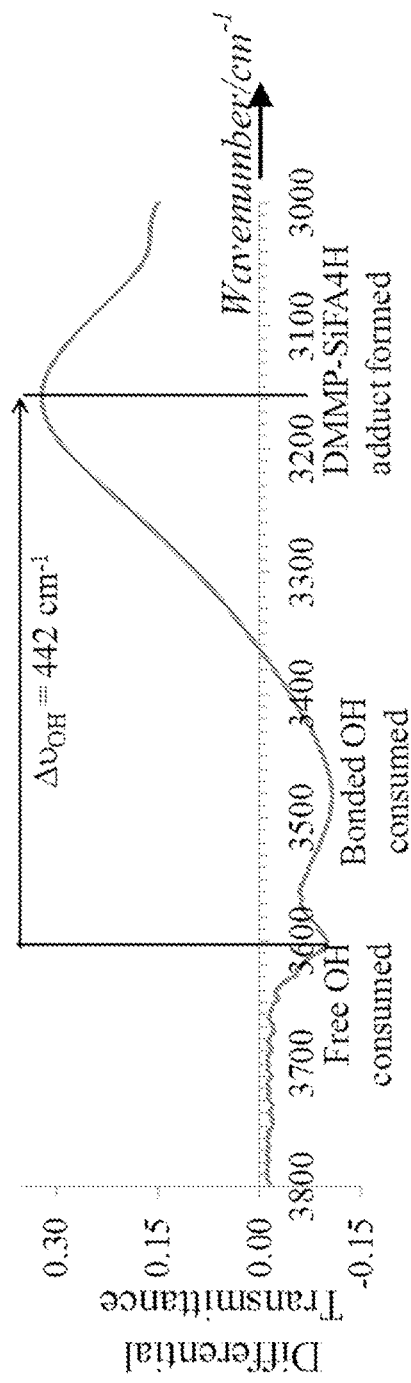
FIG. 3B shows a differential FTIR spectra for SiFA4H-DMMP HB adduct.
Figure 4:
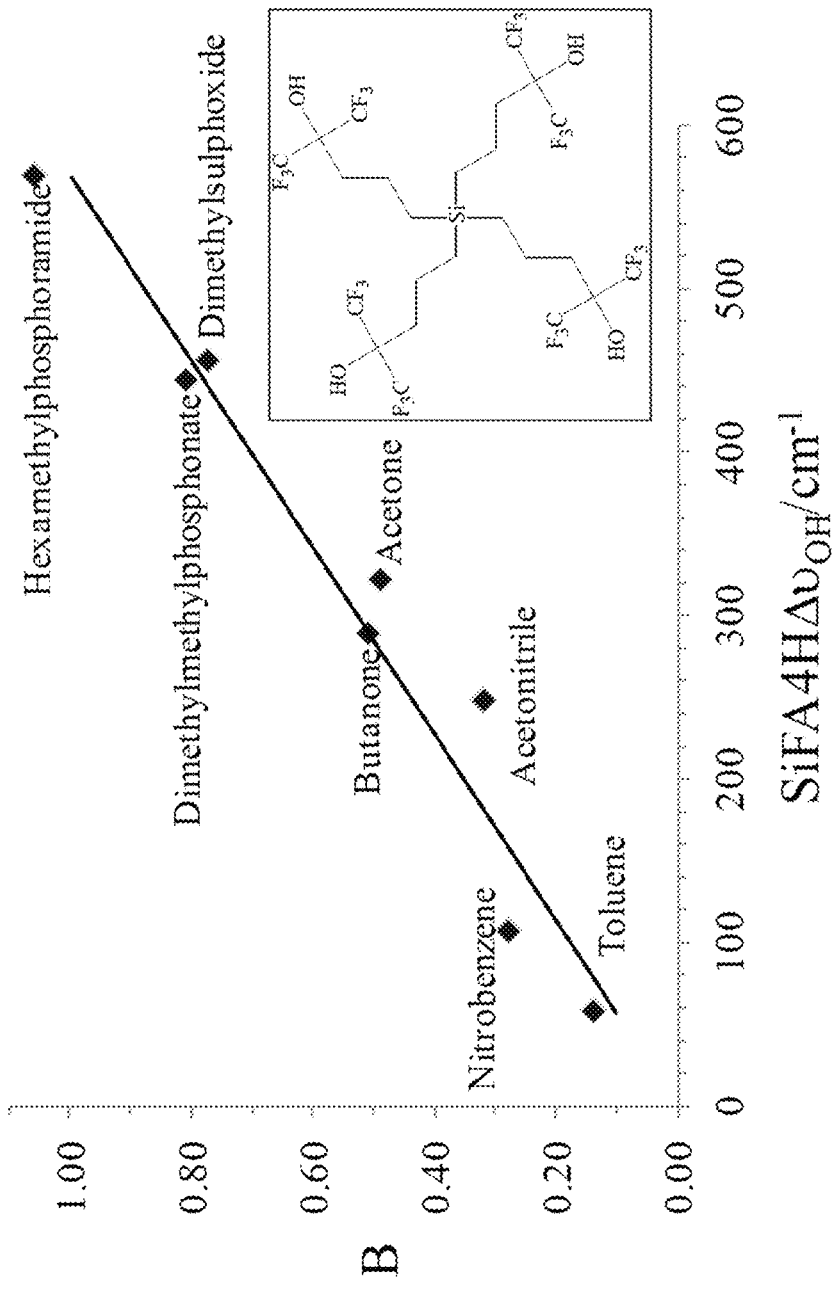
FIG. 4 shows a SiFA4H Solutochromic hydroxyl shift ($\Delta\upsilon OH$) correlated with vapor adduct HB basicity (B) and the structure of SiFA4H.

The characteristic IR absorption bands of the analytes and sorbents as separate or bonded materials are the features used to help identify individual molecules or intermolecular analyte-sorbent bonds. FIGS. 3A and 3B illustrate the effect of the vapor-polymer HB for the —OH stretch in SiFA4H, a HB acidic carbosilane sorbent. (Among the differential signal components could be the heat of sorption, which would increase the FTIR signal. While heats of sorption are non-selective, the photothermal signatures emitted provide spectral information.) The —OH IR stretching band shifts by hundreds of wavenumbers depending on the vapor-sorbent HB strength. FIG. 4 shows that the degree of shift is well correlated with the HB basicity of the vapor or gas.

One important class of TICs, the di-halogens (e.g. chlorine), are not IR active as separate species but are readily reacted to specific polymer functionalities that provide suitable IR cross sections.

IR Spectroscopy measures the vibration modes of molecules in the IR (2-16 µm) region of the spectrum. A portion of this spectrum is the so-called fingerprint region (6-14 µm) where complex signatures of molecules are present that make this region particularly suitable for sensor applications with high selectivity. Unfortunately, this is also a spectrally busy region with overlapping peaks and the performance of fitting algorithms is diminished for mixtures. To overcome this, instead of a single measurement, IR spectra are measured in multiple sorbent polymers. Due to the variations of analyte affinity towards different sorbent layers, the present invention provides several independent measurements with varying mixture concentrations. When analyzed in conjunction with spectra from along GC columns, detection algorithm performance can be greatly improved. The optical absorbance for a given sorbent polymer p at the beginning of the column (assuming $N_c$ analyte components in the mixture) is given by: $A_p(\lambda) = \alpha_p(\lambda) + \Sigma_{i=1}^{N_c} c_t^0 K_{i,p}(\alpha_i(\lambda) + \Delta\alpha_{p,i}(\lambda))$ where $\alpha_i(\lambda)$ and $\alpha_p(\lambda)$ are the IR absorbance of the analyte and the polymer before sampling, $K_{i,p}$ is the partition coefficient for analyte i in polymer p and $\Delta\alpha_{pi}(\lambda)$ is the change in polymer optical absorbance due to chemical reactions or solutochromic shifts. $c_i^0$ are the concentrations of components in air and are the only fitting parameters. For points along the column, standard GC equations apply.

ATR IR Spectroscopy

The utility of IR spectroscopy is harnessed in an attenuated total reflection (ATR) configuration, which takes advantage of the evanescent field of the light that extends ~1 µm from a reflected prism surface (FIG. 1). This small interaction depth is an ideal fit for a thin sorbent layer required for GC analysis. Other sorbent coated optical configurations for this invention are possible and are described below.

Ideally the spot size of the incident IR light would match the width of the stationary phase in the GC column and form a thin rectangular shape with the thin side of the rectangle directed along the GC column length.

Instead of employing an ATR crystal approach, the more straightforward transmission of IR light through a sorbent stationary phase can be utilized. Moreover, it is possible to include other monitoring approaches in addition to IR probe sensing (e.g. refractive index monitoring).

Multidimensional Gas Chromatography

To consider the wide range of CWA and TIC analytes of interest, multiple columns operated in parallel are included. Each column is coated with a different sorbent stationary phase. Chemosorbent stationary phases are selected to target nerve, blister, blood and other CWAs and selected TICs. Chemoreactive stationary phases are selected for those TICs not suitable for effective chromatography. In the latter case, the GC column still serves the purpose of separating chemicals not of interest away from the analyte of interest. It also functions effectively as a dosimeter record for the TIC The GC columns may be operated in parallel or sequentially. Additionally, a single column may include more than one stationary phase coating either coated in series fashion or on different interior surfaces of the column structure to form analyte competitive surfaces which can improve the selectivity of the chromatography and detection process.

The stationary phase may be deposited as a single "strip" to allow a gap between the side wall of the column. This prevents any sorbent stationary phase pooling in any column crevice or angular structures. Sorbent pooling leads to undesirable effects on GC separation performance with significant peak tailing.

The GC column can be fronted by a sorbent coated preconcentrator or sorbent coated "focusing" device which collects analyte before or at the inlet end of the GC column and is actuated by heating to release any sorbed vapors and gases into the GC column. This may simply comprise a thicker coated area at the head of the GC column which is separately heated to allow rapid thermal ramping to desired injection temperatures. Alternatively, a cryogenic trap may be positioned before or at the inlet end of the GC column.

Additionally, there can be a "smart" control mechanism upstream of the GC. The use of infrared absorption spectroscopy (IRAS) or Raman spectroscopy can be used to probe a preconcentrator or injector zone so that the GC doesn't probe or perhaps even operate until there is something of interest collected. If microfabricated, the GC could be quickly brought up to operational temperature in seconds only when needed to save on power.

After injection into a column, the column temperature may be controlled to allow elution of some analytes but essentially no column travel for other analytes. IRAS can be used to probe near the entry of the column to monitor analytes that don't move down the column and actuate heating if necessary to move analytes that are stationary at the head of the column. A "smart" GC temperature ramping system control could be used without the need for predefined isothermal column conditions, temperature ramp rates, and target temperatures. The controlled heating elements may comprise resistive cartridges, meander heater traces, and thermoelectric devices. These heating elements may be near and along the columns for changing the column temperature during analysis according to a prescribed schedule or as part of an active feedback loop based on the detector response during measurement.

The column may also have a carrier gas flow rate control mechanism. If more time is desired to examine one or more bands of chemical progressing along a column, a command can be sent to reduce the carrier gas flow rate or turn it off to halt any further progression until the carrier flow is started again.

Chemosorbent Materials

A range of commercial and custom sorbents can be used as stationary phases are including a set of hypersorbent HB acidic materials previously developed at NRL for nerve and blister CWAs. Several of these HB acidic carbosilane polymers have a demonstrated pedigree with millions of thermally cycled applications in air, demonstrating no measurable change in sorption properties. This is an important performance metric for a polar GC stationary phase operating with air as a carrier gas.

TIC Chemo-Reactive Materials

A significant number of the TICs are permanent gases under ambient conditions and because of their high vapor pressure, partitioning into polymer phases is relatively low. Other stationary phase candidates to consider include those which emphasize reactivity as either oxidizing or reducing agents and their Lewis acid or base properties. A number of the high threat TICs (HCN, HF, HCl, HBr, $H_2S$, $HNO_3$) exhibit significant Lewis acidity as gas phase species and bind well to surfaces with complimentary Lewis base properties such as alumina ($Al_2O_3$). These adducts provide IR signatures for identification. $HNO_3$ has also been shown to form nitrate salts when exposed to zinc chloride; however, this presents a more difficult path for regeneration for multiple use. Another TIC, $BF_3$, reacts in air to form HF so it may also be detected by the HF adduct to a Lewis base. The chlorine, bromine and fluorine dihalogen TICs are reactive to a number of chemistries under ambient conditions including the alkene double bonds forming dihalide structures. Polybutadiene is a suitable polymer for this purpose. The halogenated products provide suitable IR signatures for detection. Other TICs such as ammonia are naturally present at low concentrations in the environment and therefore may not be useful candidates for such reaction schemes; however, transition metal coordination chemistries for $NH_3$ and $AsH_3$ are paths to reversible IR signatures.

When using reactive sorbent chemistries that chemically bond to TICs or other hazardous chemical, changes in chemical bonding in the sorbent can be monitored. Once reacted, that portion of the GC column is not capable of reacting with the analyte of interest unless a regeneration protocol is available. The GC-IRAS system could be instructed to ignore the reacted zone and monitor further along the column (this happens inherently in a "differential" spectroscopic approach by renormalizing the start point). Chromatography is effected in the column, and the amount of reacted sites quantifies the analyte in a dosimeter fashion.

Waveguide Evanescent Field Spectroscopy

Figure 5:
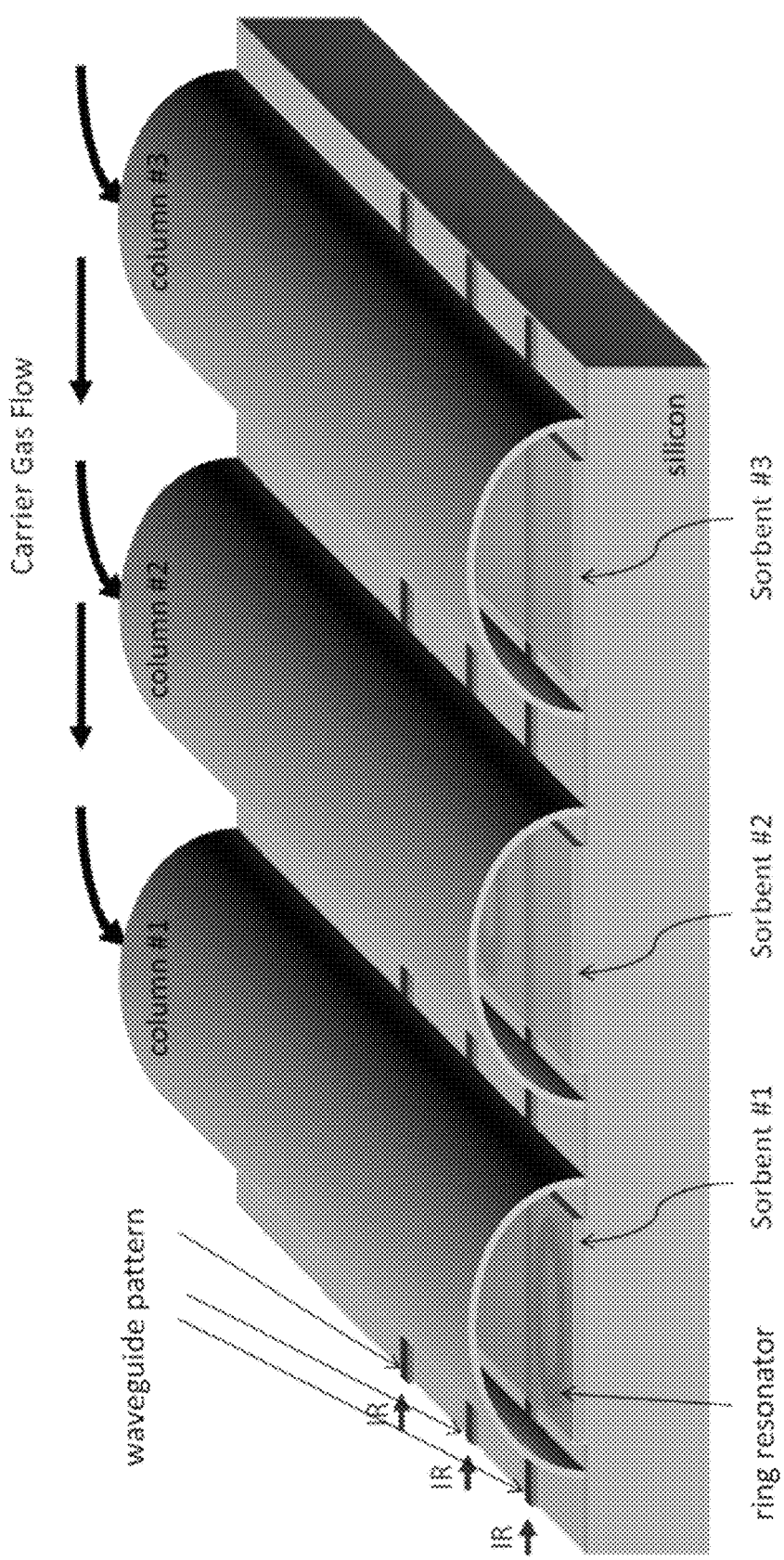
FIG. 5 shows an array of IR ring resonators positioned along a GC column or GC columns and coated with different stationary sorbent phases. Evanescent field absorption spectroscopy is used to probe each sorbent coated micro-ring resonator over a range of incident wavelengths. Preferred interrogation wavelength range is 1-10 microns. Ring resonators are operated to allow in-column monitoring of solute or analyte as it progresses along the column(s).

Instead of placing the GC column(s) on an ATR crystal, the columns can be located on a substrate that has had waveguides patterned along its surface (FIG. 5). These waveguides can be made of material that is transparent to infrared radiation, and can be patterned to bring the radiation to specific locations at the GC columns for high spatial resolution spectroscopic probing. Either tunable infrared lasers with single element detectors or broadband infrared sources with spectrally resolved detectors can be used with these waveguides. As long as the waveguides are thinner than the wavelength of the infrared radiation, strong evanescent fields will exist within the sorbent material. Microcavity waveguide resonators, such as Fabry-Perot cavities or microrings can be used to increase the effective optical interaction length without increasing the footprint size of the infrared probe. The evanescent field above the waveguide will spectroscopically probe the sorbent material in much the same way as ATR-FTIR spectroscopy. Embedding mid-IR transparent microrings under sorbent coatings in micro GC columns allows for in-column spectroscopic analysis.

Alternatives

In addition to coating the GC sorbent stationary phase on the ATR crystal or optical waveguide structures, a second stationary phase can be coated on another interior face or opposite side of the column structure. This then provides an analyte competitive sorbent phase to the optically probed sorbent phase. Analyte in the gas phase is then distributed between the 2 different sorbents. By appropriate selection of sorbents the chemical selectivity of the sorbent coated on the ATR crystal can be substantially improved.

The chemical detector can also comprise an ultraviolet (UV) or visible light source and detector directed at the stationary phase through a transparent column for examining the reflectance spectra and fluorescence spectra of the analyte bound to a chemosorbent or chemo-reactive stationary phase along the column. There are some dyes that change color in the visible light range when chemicals bind to them. These can be dissolved in a stationary phase and then when a chemical is sorbed to the polymer it binds with the dye and changes color in the visible or UV light range.

In addition to gas chromatography, a liquid chromatography configuration could also be used.

Figure 6:
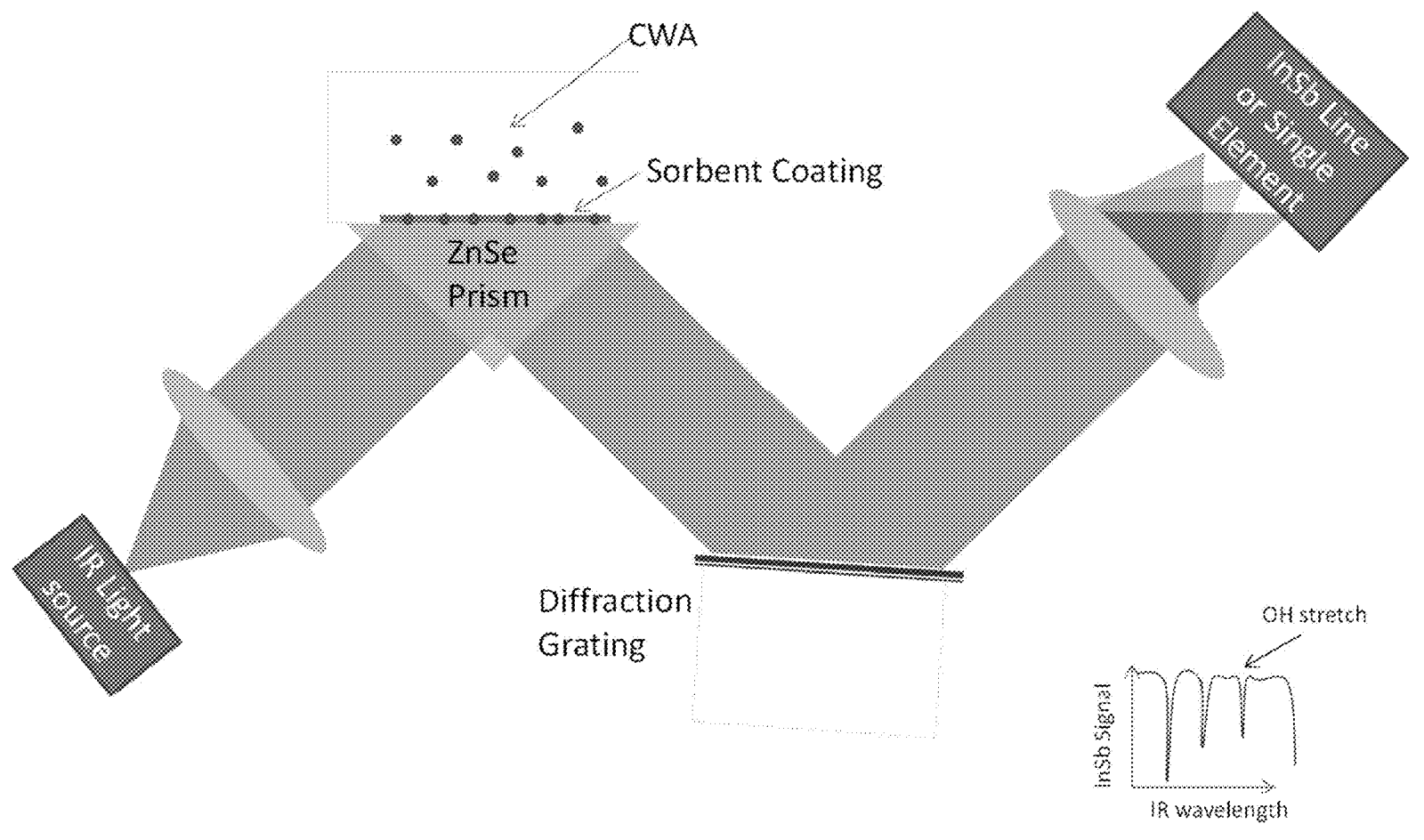
Figure 7:
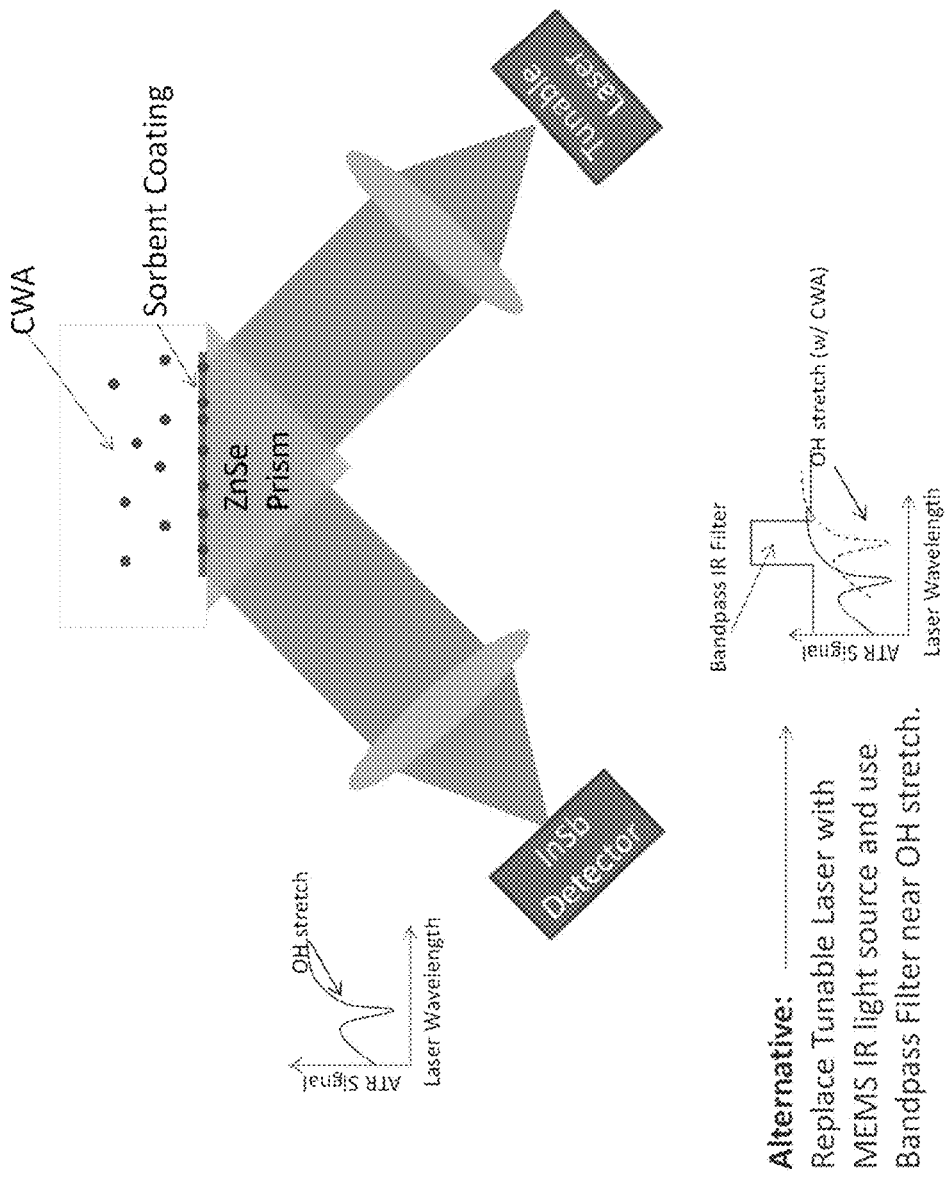
FIG. 7 shows an ATR-based sensor using a MEMS light source and a bandpass filter.

FIGS. 6-10 show alternative configurations. These may be implemented with or without the in-column GC configuration. FIG. 6 shows an ATR-based sensor using diffraction grating. FIG. 7 shows an ATR-based sensor using a MEMS light source and a bandpass filter.

Figure 8:
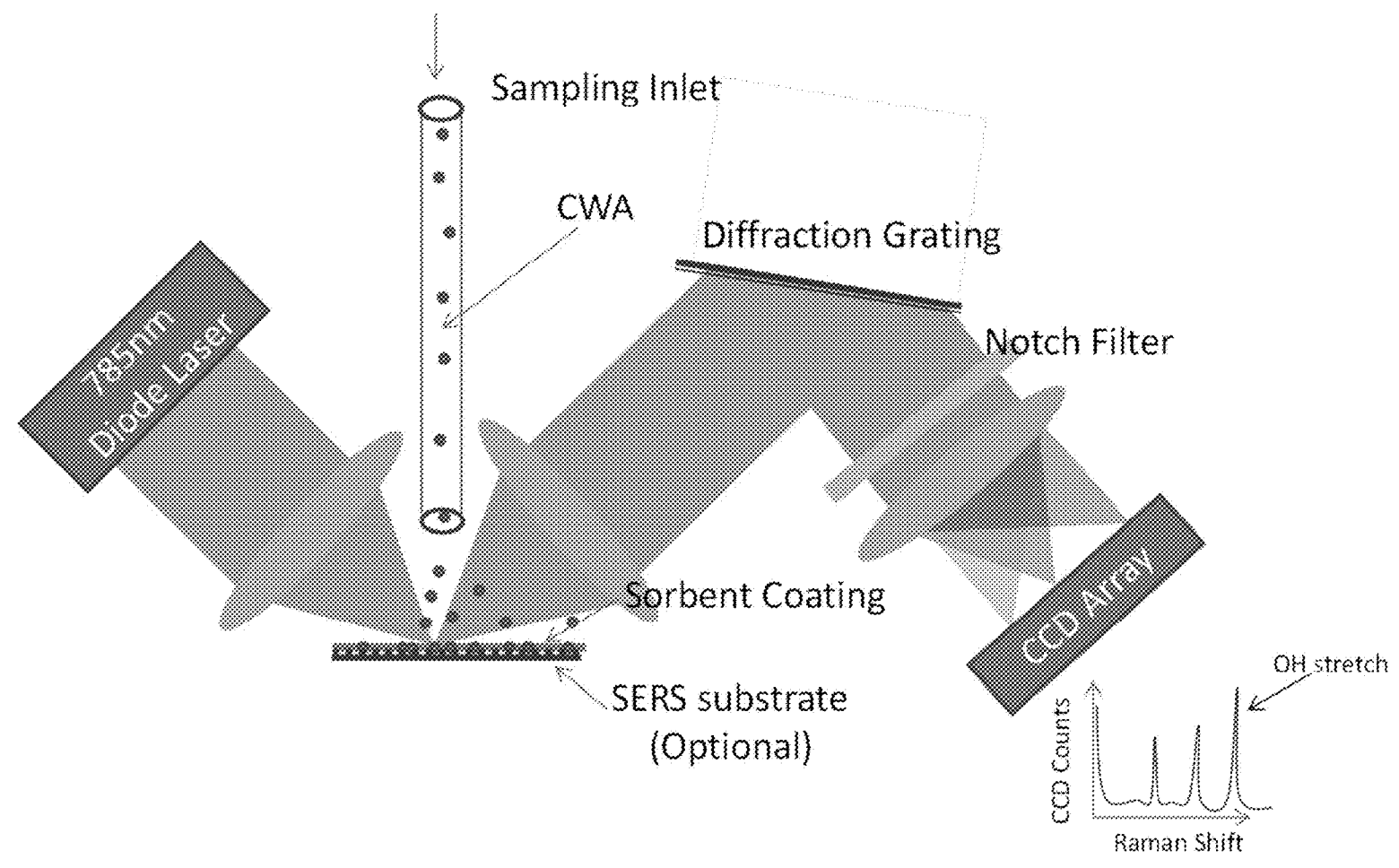

FIG. 8 shows a Raman-based sensor. In addition to probing sorbent-analyte interactions with light, a SERS configuration may be used where nano metal particles are embedded in the sorbent stationary phase and probed with a RAMAN laser and a suitable light detector.

Figure 9:
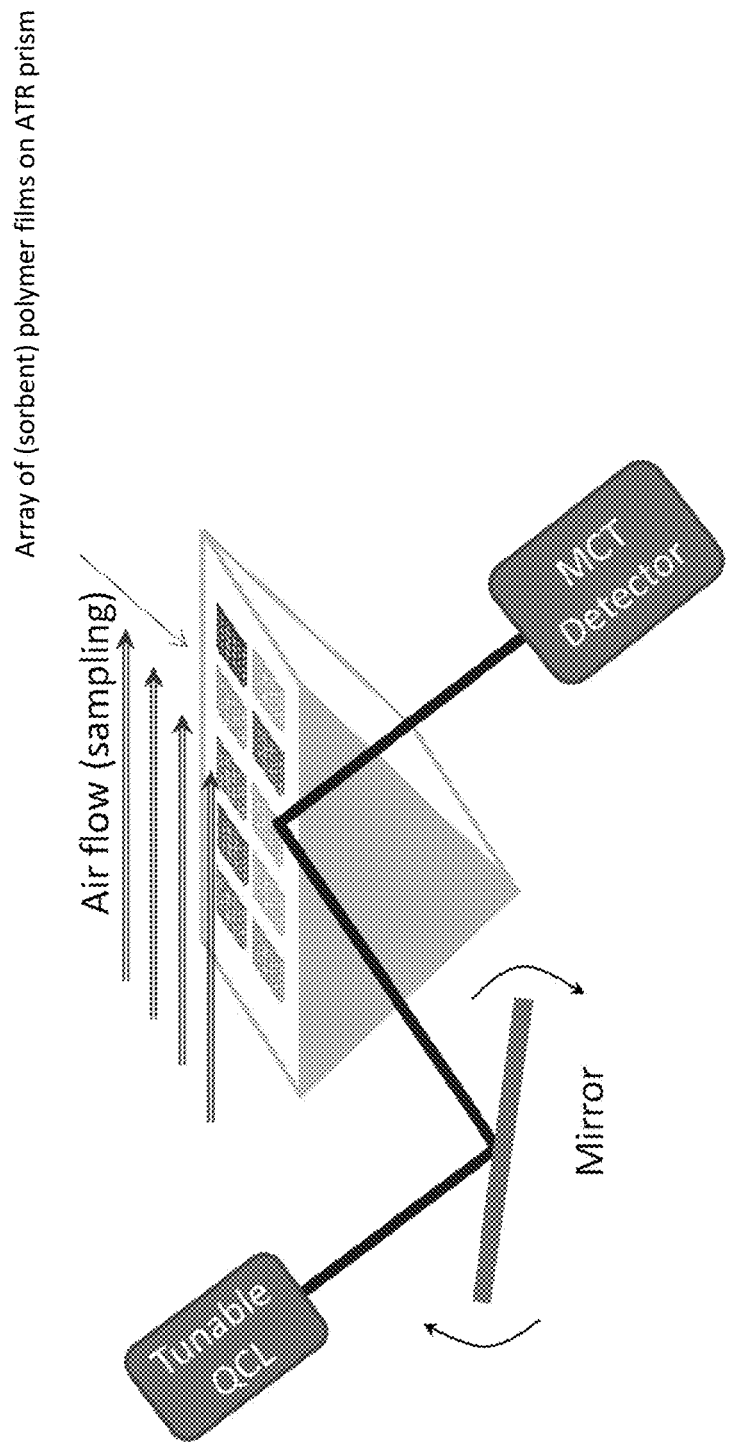
FIG. 9 shows sorbent polymer separation spectroscopy using an array of polymer films on an ATR prism.

FIG. 9 shows sorbent polymer separation spectroscopy using an array of sorbent polymer films on an ATR prism. Although not shown, platinum meander traces for joule heating (desorption) can be deposited on the surface of the prism prior to sorbent coating. These traces can be used for closed-loop temperature control.

Figure 10:
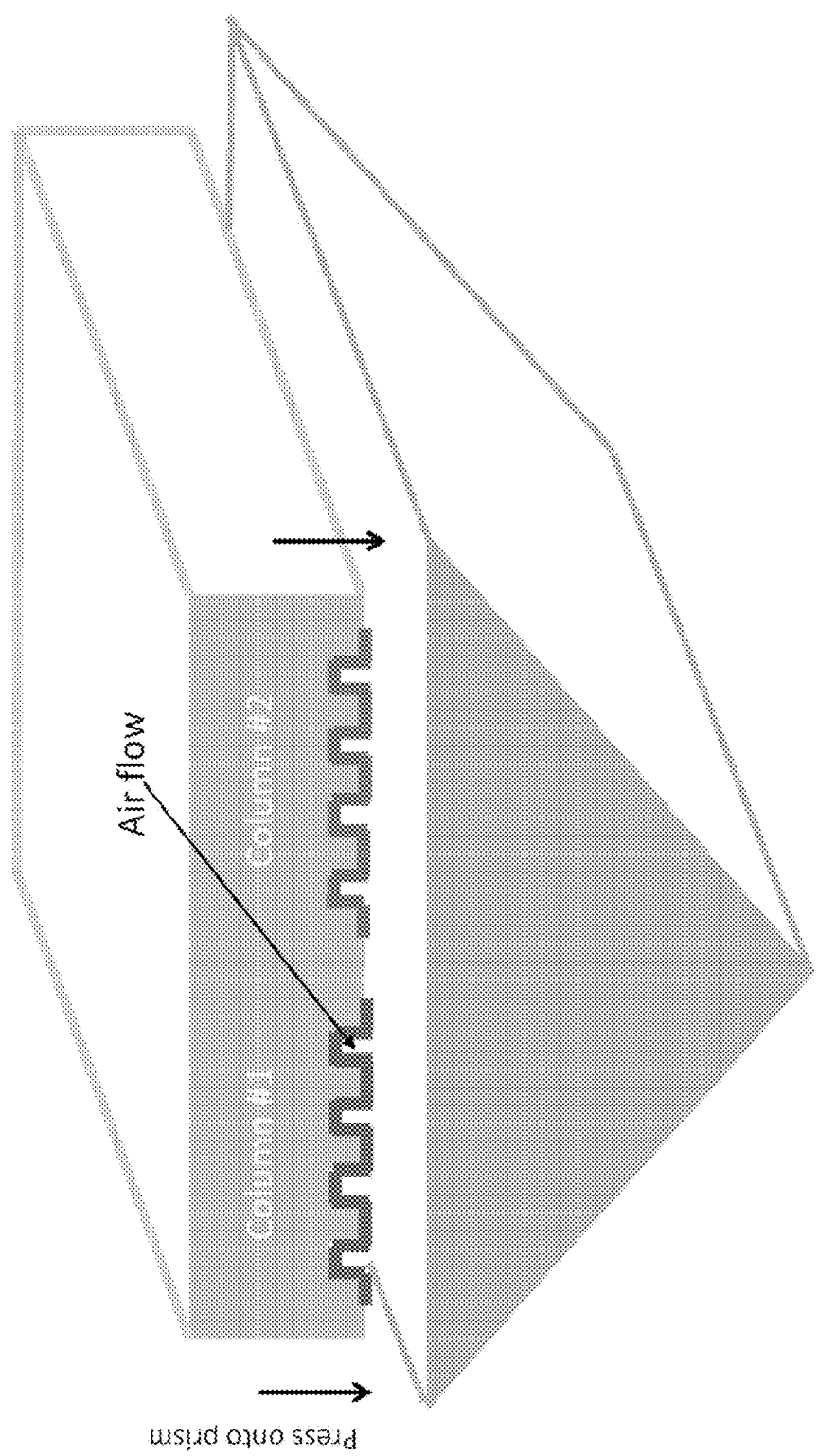
FIG. 10 shows a multi GC-IR-ATR-Spectroscopy concept of pressing and attaching a pre-coated GC cartridge onto the prism.

FIG. 10 shows a multi GC-IR-ATR spectroscopy concept using an alternative sorbent polymer deposition. A single GC column has a series of channels, which are completely coated. This GC column becomes a disposable part. To replace it, one would just wipe off any old polymer residue off of the prism and press onto the prism a new GC "cartridge" already coated with stationary phase. The grooves in the channel allow for air to flow, and the coated ridges make intimate contact with the prism and can be interrogated using ATR spectroscopy or bridge resonators.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A chemical detector for simultaneous detection of multiple chemicals including chemical warfare agents, toxic industrial chemicals, and explosives, comprising:
    an infrared-transparent base;
    one or more gas chromatography columns, wherein each column comprises one or more chemosorbent or chemo-reactive stationary phases, and wherein each column is on the infrared-transparent base;
    an infrared light source;
    a moveable mirror to direct the light source to the more than one gas chromatography columns, wherein the light source can be directed to any point along any of the columns or to a preconcentrator or collector device, wherein in-column chemical detection can occur at all points along every column; and
    an infrared sensor.

2. The chemical detector of claim 1, wherein when there is more than one column, each column is operated in parallel.

3. The chemical detector of claim 1, wherein at least one stationary phase comprises a carbosilane material with hydrogen bond acidic functionalization.

4. The chemical detector of claim 1, wherein the infrared-transparent base comprises an attenuated total reflection (ATR) crystal.

5. The chemical detector of claim 1, wherein the infrared light source comprises one or more optionally tunable infrared lasers, and more preferably the bright infrared light source comprises one or more quantum cascade lasers (QCLs).

6. The chemical detector of claim 1, additionally comprising a focusing lens used with the moveable mirror to direct the light source.

7. The chemical detector of claim 1, additionally comprising an analyte preconcentrator comprising sorbent coated structures positioned before or at the inlet end of at least one of the columns.

8. The chemical detector of claim 1, additionally comprising one or more independently controlled heating elements along one or more columns.

9. A method for simultaneous detection of multiple chemicals including chemical warfare agents, toxic industrial chemicals, and explosives, comprising:
    injecting a vapor-phase analyte sample into one or more gas chromatography columns, wherein each column comprises one or more chemosorbent or chemo-reactive stationary phases, and wherein each column is on an infrared-transparent base;
    directing an infrared light source to a point at one of the columns, wherein the light source can be directed to any point along any of the columns or to a preconcentrator or collector device, wherein in-column chemical detection can occur at all points along every column; and
    using an infrared sensor to detect for the presence of chemicals.

10. The method of claim 9, wherein when there is more than one column, each column is operated in parallel.

11. The method of claim 9, wherein at least one stationary phase comprises a carbosilane material with hydrogen bond acidic functionalization.

12. The method of claim 9, wherein the infrared-transparent base comprises an attenuated total reflection (ATR) crystal.

13. The method of claim 9, wherein the infrared light source comprises one or more optionally tunable infrared lasers, and more preferably the bright infrared light source comprises one or more quantum cascade lasers (QCL).

* * * * *